US 6,713,434 B2

(12) United States Patent
Millet et al.

(10) Patent No.: US 6,713,434 B2
(45) Date of Patent: *Mar. 30, 2004

(54) HERBICIDAL COMPOSITIONS

(75) Inventors: Jean-Claude Millet, Ecully (FR); Jairo E. Melgarejo Garcia, Apex, NC (US)

(73) Assignee: Rhone-Poulenc Agro, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/076,616

(22) Filed: Feb. 19, 2002

(65) Prior Publication Data

US 2003/0060368 A1 Mar. 27, 2003

Related U.S. Application Data

(63) Continuation of application No. 09/801,758, filed on Mar. 9, 2001, now abandoned, which is a continuation of application No. 09/264,888, filed on Mar. 9, 1999, now Pat. No. 6,214,770.

(30) Foreign Application Priority Data

Mar. 9, 1998 (GB) .............................. 9804986

(51) Int. Cl.⁷ ..................... A01N 43/824; A01N 43/80
(52) U.S. Cl. .................. 504/138; 504/139; 504/141
(58) Field of Search ................ 504/138, 139, 504/141

(56) References Cited

U.S. PATENT DOCUMENTS

| 5,656,573 A | 8/1997 | Roberts et al. ............. 504/271 |
| 5,804,532 A | 9/1998 | Cain et al. .................. 504/309 |
| 5,849,928 A | 12/1998 | Hawkins ..................... 548/248 |
| 5,900,389 A | 5/1999 | Fenderson et al. .......... 504/129 |
| 6,046,133 A | 4/2000 | Hewett et al. |

FOREIGN PATENT DOCUMENTS

| EP | 0213892 | 3/1987 |
| EP | 0418175 | 3/1991 |
| EP | 0487357 | 5/1992 |
| EP | 0496630 | 7/1992 |
| EP | 0496631 | 7/1992 |
| EP | 0527036 | 2/1993 |
| EP | 0560482 | 9/1993 |
| WO | 97/23134 | 7/1997 |
| WO | 98/56251 | 12/1998 |

OTHER PUBLICATIONS

*The Pesticide Manual*, 10th edition, The British Crop Protection Council, London, pp. 195–196, 376–378, 456–457, 490–491, 611–612, 626–627, 670–671, 709–710, 728–729, 947–948, 1108 (1994).

*Primary Examiner*—S. Mark Clardy
(74) *Attorney, Agent, or Firm*—Burns, Doane, Swecker & Mathis, L.L.P.

(57) ABSTRACT

This invention relates to the control of weeds using (a) a urea herbicide and (b) a 4-benzoylisoxazole or a 2-cyano-1,3-dione herbicide.

27 Claims, No Drawings

HERBICIDAL COMPOSITIONS

CROSS-REFERENCE TO RELATED APPLICATION AND TO PRIORITY APPLICATION

This application is a continuation of copending U.S. patent application Ser. No. 09/801,758, filed Mar. 9, 2901, now abandoned, which is a continuation of U.S. patent application Ser. No. 09/264,888, filed Mar. 9, 1999, now U.S. Pat. No. 6,214,770, both expressly incorporated by reference herein in their entireties and relied upon, and claims priority under 35 U.S.C. §119 of United Kingdom Patent Application No. 98 04986.9, filed Mar. 9, 1998, also expressly incorporated by reference herein in its entirety and relied upon.

BACKGROUND OF THE INVENTION

This invention relates to new herbicidal compositions comprising a mixture of 4-benzoylisoxazoles or 2-cyano-1,3-diones and herbicidal urea compounds. It also relates to the use of the mixture per se and to a method of controlling weeds.

Herbicidal 4-benzoylisoxazoles are disclosed in the literature, for example see European Patent Publication Nos. 0418175, 0487357, 0527036 and 0560482. Herbicidal 2-cyano-1,3-dione derivatives are known from EP 0213892, EP 0496630, EP 0496631 and EP 0560482. The first commercially available 4-benzoylisoxazole is isoxaflutole [5-cyclopropyl-4-(2-methylsulfonyl-4-trifluoromethyl)-benzoylisoxazole]. Urea herbicides are well known in the literature. Examples of such herbicides include fenuron, fluometuron, monuron, monolinuron, chlortoluron, isoproturon, diuron, linuron, neburon, methabenzthiazuron and tebuthiuron, all of which are described in the Pesticide Manual 10th edition (British Crop Protection Council).

SUMMARY OF THE INVENTION

The present invention provides a method for controlling the growth of weeds (i.e. undesired vegetation) at a locus which comprises applying to the locus an effective amount of (a) a urea herbicide, preferably a compound of the general formula (I):

$$R^{11}N(R^{12})CON(R^{13})R^{14} \quad (I)$$

wherein $R^{11}$ represents an optionally substituted cyclic hydrocarbyl (which is preferably aromatic, e.g. phenyl) or aromatic heterocyclyl (e.g. thiadiazol-2-yl) group, $R^{12}$ represents hydrogen or straight or branched chain alkyl containing from 1 to 6 carbon atoms, $R^{13}$ represents straight or branched chain alkyl containing from 1 to 6 carbon atoms or an optionally substituted cyclic hydrocarbyl (e.g. 2-methylcyclohexyl) group and $R^{14}$ represents hydrogen or straight or branched chain alkyl or alkoxy containing from 1 to 6 carbon atoms; and (b) a 4-benzoylisoxazole herbicide or a 2-cyano-1,3-dione herbicide, an enolic tautomeric form thereof, or an agriculturally acceptable salt or metal complex thereof;

which are herbicidally effective in combination.

For this purpose, the urea herbicide and (b) are normally used in the form of herbicidal compositions (i.e. in association with compatible diluents or carriers and/or surface-active agents suitable for use in herbicidal compositions), for example as hereinafter described.

DETAILED DESCRIPTION OF THE INVENTION

Preferred compounds of general formula (I) are those wherein $R^{12}$ represents the hydrogen atom or the methyl group and $R^{13}$ represents the methyl group.

Preferred compounds of general formula (I) are those wherein $R^{12}$ represents the hydrogen atom, $R^{13}$ represents a phenyl, 3-trifluoromethylphenyl or 4-chlorophenyl group and $R^{14}$ represents the methyl group; or $R^{11}$ represents a 4-chlorophenyl group and $R^{14}$ represents the methoxy group, which are known respectively as fenuron, fluometuron, monuron and monolinuron, and more especially compounds of general formula (I) wherein $R^{12}$ represents the hydrogen atom and $R^{13}$ represents the methyl group, and $R^{11}$ represents a 3-chloro-4-methylphenyl or 4-isopropylphenyl group and $R^{14}$ represents the methyl group; or $R^{11}$ represents the 3,4-dichlorophenyl group and $R^{14}$ represents methyl, methoxy or butyl; or $R^{11}$ represents the benzothiazol-2-yl group, $R^{12}$ represents methyl and $R^{13}$ represents methyl and $R^{14}$ represents hydrogen; or $R^{11}$ represents 5-t-butyl-thiadiazol-2-yl, $R^{12}$ and $R^{13}$ represent methyl and $R^{14}$ represents hydrogen; which are known respectively as chlortoluron, isoproturon, diuron, linuron, neburon, methabenzthiazuron and tebuthiuron.

Preferably (a) is tebuthiuron.

Preferably (b) is a 4-benzoylisoxazole herbicide. Preferably the 4-benzoylisoxazole has the formula (II):

(II)

wherein:

R is hydrogen or —$CO_2R^3$;

$R^1$ is $C_{1-4}$ alkyl or $C_{3-6}$ cycloalkyl optionally substituted by $C_{1-6}$ alkyl;

$R^2$ is selected from halogen, nitro, cyano, —$(CR^4R^5)_qS(O)_pR^6$, —$S(O)_pR^6$, —$N(R^7)SO_2R^6$, $C_{1-6}$ alkoxy, —$OSO_2R^6$, $C_{1-4}$ haloalkoxy, $C_{1-4}$ alkyl and $C_{1-4}$ haloalkyl, wherein $R^4$, $R^5$, $R^6$, $R^7$, p and q are as defined below;

or two groups $R^2$, on adjacent carbon atoms of the phenyl ring may, together with the carbon atoms to which they are attached, form a 5 or 6 membered saturated or unsaturated heterocyclic ring containing up to three ring heteroatoms selected from nitrogen, oxygen and sulfur, which ring may be optionally substituted by one or more groups selected from halogen, nitro, —$S(O)_pR^6$, $C_{1-4}$ alkyl, $C_{1-4}$ alkoxy, $C_{1-4}$ haloalkyl and $C_{1-4}$ haloalkoxy, wherein $R^6$ and p are as defined below, it being understood that a sulfur atom, where present in the ring, may be in the form of a group —SO— or —$SO_2$—;

n is an integer from one to five;

p is zero, one or two;

q is one or two; where q is two the groups ($CR^4R^5$) may be the same or different;

$R^3$ is $C_{1-4}$ alkyl;

$R^4$ and $R^5$ are independently hydrogen or $C_{1-4}$ alkyl;

$R^6$ is $C_{1-4}$ alkyl, or phenyl or benzyl, each of phenyl and benzyl optionally bearing from one to five substituents which may be the same or different selected from the group consisting of halogen, $C_{1-4}$ alkyl, $C_{1-4}$ alkoxy, $C_{1-4}$ haloalkyl, $C_{1-4}$ haloalkoxy, nitro and —$S(O)_pCH_3$, wherein p is as defined above;

and $R^7$ is hydrogen or $C_{1-6}$ alkyl.

In this description the term "agriculturally acceptable salts" means salts the cations or anions of which are known and accepted in the art for the formation of salts for agricultural or horticultural use. Preferably the salts are water-soluble. Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts.

It will be understood that in certain cases the groups $R^1$, $R^2$, $R^3$, $R^4$, $R^5$, $R^6$ and $R^7$ may give rise to stereoisomers and geometric isomers. All such forms are embraced by the present invention.

Throughout this description the terms "alkyl" and "alkoxy" refer to straight or branched chains. The terms "haloalkyl" and "haloalkoxy" refer to alkyl and alkoxy, respectively, each substituted by at least one halogen. The term "halogen" refers to fluorine, chlorine, bromine and iodine.

In formula (II) above, compounds in which n is three and the groups $(R^2)_n$ occupy the 2, 3 and 4-positions of the benzoyl ring; or in which n is two and the groups $(R^2)_n$ occupy the 2 and 4-positions of the benzoyl ring are preferred.

In formula (II) above, $R^2$ is preferably selected from halogen (preferably chlorine or bromine), —S(O)$_p$Me and trifluoromethyl.

In formula (II) above, preferably one of the groups $R^2$ is —S(O)$_p$Me.

Compounds of formula (II) above in which R is hydrogen are also preferred.

The compounds of formula (II) of particular interest include the following: 5-cyclopropyl-4-(2-methylsulfonyl-4-trifluoromethyl)benzoylisoxazole (isoxaflutole); 5-cyclopropyl-4-(4-methylsulfonyl-2-trifluoromethyl) benzoylisoxazole; 4-(2-chloro-4-methylsulfonyl)benzoyl-5-cyclopropylisoxazole; 4-(4-chloro-2-methylsulfonyl) benzoyl-5-cyclopropylisoxazole; 4-(4-bromo-2-methylsulfonyl)benzoyl-5-cyclopropylisoxazole; and ethyl 5-cyclopropyl-4-(2-methylsulfonyl-4-trifluoromethyl) benzoylisoxazole-3-carboxylate.

When component (b) is a 2-cyano-1,3-dione derivative, it is generally a compound of formula (III):

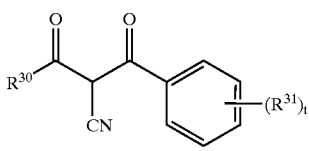

(III)

wherein:
$R^{30}$ is $C_{1-4}$ alkyl or $C_{3-6}$ cycloalkyl optionally substituted by $C_{1-6}$ alkyl;

$R^{31}$ is selected from halogen, nitro, cyano, —S(O)$_r R^{32}$, —(CR$^{33}$R$^{34}$)$_v$S(O)$_r R^{32}$, —N(R$^{35}$)SO$_2$R$^{32}$, $C_{1-6}$ alkoxy, —OSO$_2$R$^{32}$, $C_{1-4}$ haloalkoxy, $C_{1-4}$ alkyl and $C_{1-4}$ haloalkyl;

or two groups $R^{31}$, on adjacent carbon atoms of the phenyl ring may, together with the carbon atoms to which they are attached, form a 5 or 6 membered saturated or unsaturated heterocyclic ring containing up to three ring heteroatoms selected from nitrogen, oxygen and sulfur, which ring may be optionally substituted by one or more groups selected from halogen, nitro, —S(O)$_r$ R$^{32}$, $C_{1-4}$ alkyl, $C_{1-4}$ alkoxy, $C_{1-4}$ haloalkyl and $C_{1-4}$ haloalkoxy, it being understood that a sulfur atom, where present in the ring, may be in the form of a group —SO— or —SO$_2$—;

t is an integer from one to five (preferably one, two or three);

r is zero, one or two;

$R^{32}$ is $C_{1-4}$ alkyl, or phenyl or benzyl, each of phenyl and benzyl optionally bearing from one to five substituents which may be the same or different selected from the group consisting of halogen, $C_{1-4}$ alkyl, $C_{1-4}$ alkoxy, $C_{1-4}$ haloalkyl, $C_{1-4}$ haloalkoxy, nitro and —S(O)$_r$CH$_3$;

$R^{33}$, $R^{34}$ and $R^{35}$ are independently hydrogen or $C_{1-4}$ alkyl;

v is one or two; where v is two the groups (CR$^{33}$R$^{34}$) may be the same or different;

an enolic tautomeric form thereof, or an agriculturally acceptable salt or metal complex thereof.

It will be understood that the compounds of formula (III) may exist in enolic tautomeric forms that may give rise to geometric isomers around the enolic double bond. Furthermore, in certain cases the groups $R^{30}$ to $R^{32}$ may give rise to stereoisomers and geometric isomers. All such forms are embraced by the present invention. By the term "metal complexes" is meant compounds in which one or both of the oxygen atoms forming part of a 1,3-dione in formula (II) act as chelating agents to a metal cation. Examples of such cations include zinc, manganese, cupric, cuprous, ferric, ferrous, titanium and aluminum. It will be understood that in the description that follows, reference to compounds of formula (II) includes agriculturally acceptable salts, metal complexes or enolic tautomeric forms thereof.

$R^{30}$ is preferably 1-methylcyclopropyl or, most preferably, cyclopropyl.

$R^{31}$ is preferably selected from halogen (preferably chlorine or bromine), —S(O)$_r$Me, trifluoromethyl, $C_{1-4}$ haloalkoxy, $C_{1-4}$ alkoxy and —CH$_2$S(O)$_r$Me.

Preferably t is two or three. Compounds of formula (III) in which either t is three and the groups $(R^{31})_t$ occupy the 2,3 and 4-positions of the benzoyl ring; or in which t is two and the groups $(R^{31})_t$ occupy the 2 and 4-positions of the benzoyl ring; are preferred. Preferably one of the groups $R^{31}$ is —S(O)$_r$Me.

Compounds of formula (III) of particular interest include 3-cyclopropyl-2-cyano-1-(2-methylsulfonyl-4-trifluoromethylphenyl)propan-1,3-dione; 1-(2-chloro-4-methylsulfonylphenyl)-2-cyano-3-cyclopropylpropan-1,3-dione; 2-cyano-3-cyclopropyl-1-(4-fluoro-3-methoxy-2-methylsulfonylphenyl)propan-1,3-dione; 2-cyano-1-(4-methylsulfonyl-2-trifluoromethylphenyl)-3-(1-methylcyclopropyl)propan-1,3dione; and 1-(4-chloro-2-methylsulfonylphenyl)-2-cyano-3-cyclopropylpropan-1,3-dione. Most preferably the compound of formula (III) is 2-cyano-3-cyclopropyl-1-(4-fluoro-3-methoxy-2-methylsulfonylphenyl)propan-1,3-dione.

The amounts of the urea herbicide and (b) applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates of from about 500 g to 2500 g of the urea herbicide and from about 10 g to about 500 g of (b) per hectare give good results. However, it is to be understood that higher or lower application rates may be used, depending upon the particular problem of weed control encountered.

The urea herbicide and (b) in combination may be used to control selectively the growth of weeds, for example to control the growth of those species hereinafter mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, rye, maize and rice, soya beans, field and dwarf beans, peas, lucerne, cotton, peanuts, flax, onions, carrots, oilseed rape, sunflower, and permanent or sown grassland before or after sowing of the crop or before or after emergence of the crop. For the selective control of weeds at a locus of weed infestation which is an area used, or to be used, for the growing of crops, e.g. the crops hereinbefore mentioned, application rates of from about 500 g to about 2500 g of the urea herbicide and from about 25 g to about 200 g of (b) per hectare are particularly suitable.

The method described above may be used to control a very wide spectrum of annual broad-leafed weeds and grass weeds. Examples of weeds which may be controlled include:

broad-leafed weeds, for example, *Abutilon theophrasti, Amaranthus hybridus, Amaranthus retroflexus, Amaranthus rudis, Amaranthus tuberculatos, Ambrosia artemisiifolia, Ambrosia trifida, Bidens pilosa, Chenopodium album, Convolvulus arvensis, Datura ferox, Datura stramonium,* Euphorbia spp, *Galium aparine,* Helianthus spp, Ipomoea spp, e.g. *Ipomoea purpurea,* Lamium spp, Matricaria spp, Plantago spp, *Polygonum aviculare, Polygonum pennsylvanicum, Raphanus raphanistrum, Schkuhria pinnata, Sesbania exaltata, Sida rhombifolia, Sida spinosa, Sinapis arvensis, Solanum nigrum, Veronica hederaefolia, Veronica persica,* and *Xanthium strumarium,* and grass weeds, for example *Alopecurus myosuroides, Avena fatua, Brachiaria plantaginea, Cenchrus echinatus, Cynodon dactylon, Digitaria horizontalis, Digitaria sanguinalis, Echinochloa crus-galli, Eragrostis virescens, Sorghum bicolor, Eleusine indica, Imperata cylindrica, Panicum dichotomiflorum, Panicum maximum, Panicum miliaceum, Pennisetum glaucum,* Setaria spp, e.g. *Setaria faberii, Setaria viridis, Setaria lutescens and Setaria italica, Sorghum halepense,* and sedges, for example, *Cyperus esculentus.*

Where the locus is an area used, or to be used, for the growth of cereal crop preferably the urea herbicide is isoproturon or chlorotoluron.

Where the locus is an area used, or to be used, for the growth of sugarcane, or for total weed control, the urea herbicide is preferably tebuthiuron.

The following table summarizes dose rate of the components generally and preferably in the method of the invention (all dose rates are in grams per hectare (g/ha):

(a) is tebuthiuron) preferred third partners include diuron and ametryne. Preferred combinations include the following:

(i) from 1000 to 1500 g/ha of (a) (preferably from 1400 to 1500 g/ha); from 50 to 75 g/ha of (b) and from 100 to 150 g/ha of diflufenican;

(ii) from 1000 to 1500 g/ha of (a) (preferably about 1000 g/ha); from 50 to 75 g/ha of (b) and from 100 to 150 g/ha of diflufenican;

(iii) from 1000 g/ha of (a); from 100 to 150 g/ha of (b); and from 1000 to 1500 g/ha (preferably about 1250 g/ha) of diuron or ametryne.

The invention also provides synergistic herbicidal compositions comprising:

(a) a urea herbicide, preferably a compound of the general formula (I) above; and (b) a 4-benzoylisoxazole herbicide or a 2-cyano-1,3-dione herbicide, an enolic tautomeric form thereof, or an agriculturally acceptable salt or metal complex thereof;

in association with an agriculturally acceptable diluent and/or carrier.

Generally the active ingredients are homogeneously dispersed in other components cited hereinafter, such as a diluent or carrier and/or surface-active agents.

The term "herbicidal compositions" is used in a broad sense, to include not only compositions which are ready for use as herbicides but also concentrates which must be diluted before use. Preferably the compositions contain from 0.05 to 90% by weight of (a) and (b).

The herbicidal composition may contain solid and liquid carriers and surface-active agents (e.g. wetters, dispersants or emulsifiers alone or in combination). Surface-active agents that may be present in the herbicidal compositions of the present invention may be of the ionic or non-ionic types, for example sulforicinoleates, quaternary ammonium derivatives, products based on condensates of ethylene oxide with nonyl- or octyl-phenols, or carboxylic acid esters of anhydrosorbitols which have been rendered soluble by etherification of the free hydroxy groups by condensation with ethylene oxide, alkali and alkaline earth metal salts of sulfuric acid esters and sulfonic acids such as dinonyl- and dioctyl-sodium sulfono-succinates and alkali and alkaline earth metal salts of high molecular weight sulfonic acid derivatives such as sodium and calcium lignosulfonates. Examples of suitable solid diluents or carriers are aluminum silicate, talc, calcined magnesia, kieselguhr, tricalcium phosphate, powdered cork, absorbent carbon black and clays such as kaolin and bentonite. Examples of suitable liquid

| COMPONENT | CROP | TIMING | GENERAL | PREFERRED | MORE PREFERRED | MOST PREFERRED |
|---|---|---|---|---|---|---|
| (b) | sugarcane | pre-em | 50–150 | 75–150 | 75–150 | 100 |
| (b) | sugarcane | post-em | 50–150 | 75–100 | 75–100 | 100 |
| Tebuthiuron | sugarcane | pre/post | 500–1500 | 1000–1500 | 1000 | 1000 |
| (b) | Total | pre/post | 75–200 | 100–150 | 100–150 | — |
| Tebuthiuron | Total | pre/post | 500–2500 | 100–2000 | 1500 | — |
| (b) | Cereal | pre-em | 50–200 | 100–200 | 150 | — |
| (b) | Cereal | post-em | 50–100 | 50–100 | 75 | — |
| Isoproturon | Cereal | pre/post | 750–2500 | 1000–2000 | 1500 | — |
| Chlortoluron | Cereal | pre/post | 1000–2000 | 1200–1600 | 1400 | — |

Where the method of the invention is used for the control of weeds at a cereal locus in a preferred embodiment (especially where (a) is isoproturon or chlortoluron), a third herbicide is provided, preferably selected from bifenox and diflufenican. When the locus is sugarcane (especially where diluents include water, acetophenone, cyclohexanone, isophorone, toluene, xylene, and mineral, animal, and vegetable oils (these diluents may be used alone or in combination).

Herbicidal compositions according to the present invention may also contain, if desired, conventional adjuvants such as adhesives, protective colloids, thickeners, penetrating agents, stabilizers, sequestering agents, anti-caking agents, coloring agents and corrosion inhibitors. These adjuvants may also serve as carriers or diluents.

Preferred herbicidal compositions according to the present invention are wettable powders or water dispersible granules. Most preferred herbicidal compositions are aqueous suspension concentrates.

The wettable powders (or powders for spraying) usually contain from 20 to 95% of the combination, and they usually contain, in addition to the solid vehicle, from 0 to 5% of a wetting agent, from 3 to 10% of a dispersant agent and, if necessary, from 0 to 10% of one or more stabilizers and/or other additives such as penetrating agents, adhesives or anti-caking agents and colorings.

The aqueous suspension concentrates, which are applicable by spraying, are prepared in such a way as to obtain a stable fluid product (by fine grinding) which does not settle out and they usually contain from 10 to 75% of the combination, from 0.5 to 15% of surface acting agents, from 0.1 to 10% of thixotropic agents, from 0 to 10% of suitable additives such as antifoams, corrosion inhibitors, stabilizers, and water or an organic liquid in which the active substance is sparingly soluble or insoluble. Some organic solid substances or inorganic salts can be dissolved in order to assist in preventing sedimentation or as antifreeze for the water.

Herbicidal compositions according to the present invention may also comprise (a) and (b) in association with, and preferably homogeneously dispersed in, one or more other pesticidally active compounds and, if desired one or more compatible pesticidally acceptable diluents and carriers.

Examples of other pesticidally active ingredients include fungicides, insecticides, plant growth regulators and, most preferably, herbicides. Examples of additional herbicides which may be present include the following (a mixture of urea herbicides may be used in the invention): chloroacetamides (e.g. metolachlor, acetochlor, alachlor), sulfonylureas, thiocarbamates, dithiocarbamates, metribuzin, sulfentrazone, flumetsulam, clorasulam-methyl, oxasulfuron, flumiclorac, bentazon, chlorimuron, linuron, clomazone, dimethenamid, pendimethalin, trifluralin, clethodim and acifluorfen, bifenox, diflufenican, diuron, atrazine and ametryne.

A product comprising (a) a urea herbicide and (b) a 4-benzoylisoxazole herbicide or a 2-cyano-1,3-dione herbicide (or an enolic tautomeric form thereof, or an agriculturally acceptable salt or metal complex thereof) for simultaneous, separate or sequential application in controlling the growth of weeds at a locus, is also provided by the invention.

The following examples illustrate the invention without limiting it.

EXAMPLE 1

The following test was conducted in Brazil: Tebuthiuron (used as the commercial formulation "Combine™", a suspension concentrate containing 1.0 l/ha active ingredient) and 5-cyclopropyl-4-(2-methylsulfonyl-4-trifluoromethyl) benzoylisoxazole (isoxaflutole, hereafter referred to as Compound A), which was formulated as wettable granules, were sprayed alone and in tank mix combination (spray rate 300 l/ha) to a plot 5 meters by 3 meters pre-emergence of the weeds and ratoon sugarcane (varieties RB72 454 and RB83 5089). The soil was a heavy clay soil containing 1.8% organic matter, 69% sand and 28% clay (pH 5.3) and had been sown on the same day as application with the weed species (the application was made to the ratoon cane about 90 days after cutting and before re-growth). Visual assessment was made 95 days after treatment in comparison with an untreated control plot. Two replicates were performed.

The results were as follows (in the Table that follows the weed and crops are represented by their Bayer codes):

| COMBINATION | DOSE RATE (g/ha) | AMASP | BRAPL | DIGHO | ECHCG | ELEIN | PANMA | SACOF RB72 454 | SACOF RB68 5089 |
|---|---|---|---|---|---|---|---|---|---|
| Cpd A | 150 | 80 | 70 | 75 | 50 | 85 | 85 | 0 | 0 |
| Tebuthiuron | 500 | 75 | 10 | 10 | 10 | 20 | 5 | 0 | 0 |
| Tebuthiuron + Cpd A | 500 + 150 | 98 | 95 | 95 | 80 | 95 | 95 | 0 | 0 |
| Colby expected | | 95 | 73 | 77.5 | 55 | 88 | 85.8 | 0 | 0 |

EXAMPLE 2

The following test was conducted in Brazil following the same procedure as described in Example 1 above but where the soil type was light sandy containing 1.8% organic matter, 82% sand and 13% clay (pH 5.3). Again, two replicates were performed.

The results were as follows (in the Table that follows the weed and crops are represented by their Bayer codes):

| COMBINATION | DOSE (g/ha) | AMASP | BRAPL | DIGHO | ECHCG | ELEIN | SIDRH | SACOF RB72 454 | SACOF RB68 5089 |
|---|---|---|---|---|---|---|---|---|---|
| Cpd A | 150 | 27.5 | 15 | 20 | 20 | 30 | 10 | 0 | 0 |
| Tebuthiuron | 500 | 70 | 20 | 20 | 15 | 20 | 60 | 0 | 0 |
| Tebuthiuron + Cpd A | 500 + 150 | 95 | 90 | 90 | 80 | 90 | 92.5 | 0 | 0 |
| Colby expected | | 78.3 | 32 | 36 | 32 | 44 | 64 | 0 | 0 |

What is claimed is:

1. A composition comprising a synergistic herbicidally effective amount of:
   (a) a urea herbicide having the formula (I)

$$R^{11}N(R^{12})CON(R^{13})R^{14} \quad (I)$$

wherein $R^{11}$ represents an optionally substituted phenyl or thiadiazol-2-yl group, $R^{12}$ represents hydrogen or straight or branched chain alkyl having from 1 to 6 carbon atoms, $R^{13}$ represents straight or branched chain alkyl having from 1 to 6 carbon atoms or a 2-methylcyclohexyl group and $R^{14}$ represents hydrogen or straight or branched chain alkyl or alkoxy having from 1 to 6 carbon atoms with the exception of diuron; and
   (b) a 4-benzoylisoxazole herbicide or a 2-cyano-1,3-dione herbicide, an enolic tautomeric form thereof, or an agriculturally acceptable salt or metal complex thereof;
   in association with an agriculturally acceptable diluent and/or carrier;
   wherein the urea herbicide of (a) and the 4-benzoylisoxazole herbicide or 2-cyano-1,3-dione herbicide, enolic tautomeric form thereof, or agriculturally acceptable salt or metal complex thereof of (b) have a synergistic herbicidal effect.

2. A composition according to claim 1 wherein, in formula (I), $R^{12}$ represents hydrogen or methyl, $R^{13}$ represents phenyl, methyl, 3-trifluoromethylphenyl or 4-chlorophenyl and $R^{14}$ represents methyl.

3. A composition according to claim 1 wherein, in formula (I), $R^{11}$ represents 4-chlorophenyl, 3-chloro-4-methylphenyl, 3,4-dichlorophenyl or 4-isopropylphenyl and $R^{14}$ represents methyl, methoxy or butyl.

4. A composition according to claim 1 wherein, in formula (I), $R^{11}$ represents benzothiazol-2-yl or 5-t-butyl-thiadiazol-2-yl; $R^{12}$ and $R^{13}$ represent methyl and $R^{14}$ represents hydrogen.

5. A composition according to claim 1, wherein (a) is tebuthiuron.

6. A composition according to claim 1, wherein (b) is a 4-benzoylisoxazole herbicide of formula (II):

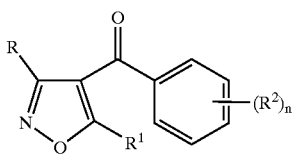

wherein:
R is hydrogen or $-CO_2R^3$;
$R^1$ is $C_{1-4}$ alkyl, or $C_{3-6}$ cycloalkyl optionally substituted by $C_{1-6}$ alkyl;
$R^2$ is halogen, nitro, cyano, $-(CR^4R^5)_qS(O)_pR^6$, $-S(O)_pR^6$, $-N(R^7)SO_2R^6$, $C_{1-6}$ alkoxy, $-OSO_2R^6$, $C_{1-4}$ haloalkoxy, $C_{1-4}$ alkyl or $C_{1-4}$ haloalkyl, wherein $R^4$, $R^5$, $R^6$, $R^7$, p and q are as defined below;
or two groups $R^2$, on adjacent carbon atoms of the phenyl ring, together with the carbon atoms to which they are attached, form a 5 or 6 membered saturated or unsaturated heterocyclic ring having up to three ring heteroatoms selected from the group consisting of nitrogen, oxygen and sulfur, which ring is optionally substituted by one or more members selected from the group consisting of halogen, nitro, $-S(O)_pR^6$, $C_{1-4}$ alkyl, $C_{1-4}$ alkoxy, $C_{1-4}$ haloalkyl and $C_{1-4}$ haloalkoxy, wherein $R^6$ and p are as defined below, it being understood that a sulfur atom, when present in the ring, is optionally in the form of a group $-SO-$ or $-SO_2-$;
n is an integer from one to five;
p is zero, one or two;
q is one or two; when q is two, the groups $(CR^4R^5)$ are the same or different;
$R^3$ is $C_{1-4}$ alkyl;
$R^4$ and $R^5$ are independently hydrogen or $C_{1-4}$ alkyl;
$R^6$ is $C_{1-4}$ alkyl, phenyl or benzyl, each of phenyl and benzyl optionally having from one to five substituents which are the same or different selected from the group consisting of halogen, $C_{1-4}$ alkyl, $C_{1-4}$ alkoxy, $C_{1-4}$ haloalkyl, $C_{14}$ haloalkoxy, nitro and $-S(O)_pCH_3$, wherein p is as defined above;
and $R^7$ is hydrogen or $C_{1-6}$ alkyl.

7. A composition according to claim 6, wherein n is two or three and the groups $(R^2)_n$ occupy the 2, 3 and 4-positions of the benzoyl ring.

8. A composition according to claim 6, wherein $R^2$ is halogen, $-S(O)_pCH_3$ or trifluoromethyl.

9. A composition according to claim 8, wherein one of the groups $R^2$ is $-S(O)_pCH_3$.

10. A composition according to claim 6, wherein R is hydrogen.

11. A composition according to claim 6, wherein (b) is:
5-cyclopropyl-4-(2-methylsulfonyl-4-trifluoromethyl)benzoylisoxazole (isoxaflutole);
5-cyclopropyl-4-(4-methylsulfonyl-2-trifluoromethyl)benzoylisoxazole;
4-(2-chloro-4-methylsulfonyl)benzoyl-5-cyclopropylisoxazole;
4-(4-chloro-2-methylsulfonyl)benzoyl-5-cyclopropylisoxazole; 4-(4-bromo-2-methylsulfonyl)benzoyl-5-cyclopropylisoxazole; or ethyl 5-cyclopropyl-4-(2-methylsulfonyl-4-trifluoromethyl)benzoylisoxazole-3-carboxylate.

12. A composition according to claim 1, wherein (b) is a 2-cyano-1,3-dione derivative of formula (III):

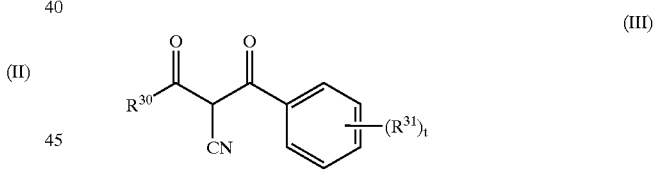

wherein:
$R^{30}$ is $C_{1-4}$ alkyl or $C_{3-6}$ cycloalkyl, optionally substituted by $C_{1-6}$ alkyl;
$R^{31}$ is halogen, nitro, cyano, $-S(O)_rR^{32}$, $-(CR^{33}R^{34})_xS(O)_rR^{32}$, $-N(R^{35})SO_2R^{32}$, $C_{1-6}$ alkoxy, $-OSO_2R^{32}$, $C_{1-4}$ haloalkoxy, $C_{1-4}$ or $C_{1-4}$ haloalkyl;
or two groups $R^{31}$, on adjacent carbon atoms of the phenyl ring, together with the carbon atoms to which they are attached, form a 5 or 6 membered saturated or unsaturated heterocyclic ring having up to three ring heteroatoms selected from the group consisting of nitrogen, oxygen and sulfur, which ring is optionally substituted by one or more members selected from the group consisting of halogen, nitro, $-S(O)_rR^{32}$, $C_{1-4}$ alkyl, $C_{1-4}$ alkoxy, $C_{1-4}$ haloalkyl and $C_{1-4}$ haloalkoxy, it being understood that a sulfur atom, when present in the ring, is optionally in the form of a group $-SO-$ or $-SO_2-$;
t is an integer from one to five;
r is zero, one or two;

$R^{32}$ is $C_{1-4}$ alkyl, phenyl or benzyl, each of phenyl and benzyl optionally having from one to five substituents which are the same or different selected from the group consisting of halogen, $C_{1-4}$ alkyl, $C_{1-4}$ haloalkyl, $C_{1-4}$ haloalkoxy, nitro and —$S(O)_rCH_3$;

$R^{33}$, $R^{34}$ and $R^{35}$ are independently hydrogen or $C_{1-4}$ alkyl;

v is one or two; when v is two, the groups ($CR^{33}R^{34}$) are the same or different;

an enolic tautomeric form thereof, or an agriculturally acceptable salt or metal complex thereof.

13. A composition according to claim 12, wherein $R^{30}$ is 1-methylcyclopropyl or cyclopropyl.

14. A composition according to claim 12, wherein $R^{31}$ is halogen, —$S(O)_rCH_3$, trifluoromethyl, $C_{1-4}$ haloalkoxy, $C_{1-4}$ alkoxy and —$CH_2S(O)_rCH_3$.

15. A composition according to claim 12, wherein t is two or three.

16. A composition according to claim 12, wherein one of the groups $R^{31}$ is —$S(O)_rCH_3$.

17. A composition according to claim 12, wherein t is two or three and the groups ($R^{31}$)$_t$ occupy the 2, 3 and 4-positions of the benzoyl ring, or the 2- and 4- positions of the benzoyl ring.

18. A composition according to claim 12, wherein (b) is: 3-cyclopropyl-2-cyano-1-(2-methylsulfonyl-4-trifluoromethylphenyl)propan-1,3-dione; 1-(2-chloro-4-methylsulfonylphenyl)-2-cyano-3-cyclopropylpropan-1,3-dione; 2-cyano-3-cyclopropyl-1-(4-fluoro-3-methoxy-2-methylsulfonylphenyl)propan-1,3-dione; 2-cyano-1-(4-methylsulfonyl-2-trifluoromethylphenyl)-3-(1-methylcyclopropyl)propan-1,3-dione; or 1-(4-chloro-2-methylsulfonylphenyl)-2-cyano-3-cyclopropylpropan-1,3-dione or 2-cyano-3-cyclopropyl-1-(4-fluoro-3-methoxy-2-methylsulfonylphenyl)propan-1,3-dione.

19. A method for controlling the growth of weeds at a locus which comprises applying to said locus a synergistic herbicidally effective amount of (a) a urea herbicide as defined in claim 1 and (b) a 4-benzoylisoxazole herbicide or a 2-cyano-1,3-dione herbicide, or an enolic tautoineric form thereof or an agriculturally acceptable salt or metal complex or mixture thereof.

20. A method according to claim 19, wherein from 500 g to 2500 g of (a) and from 10 g to about 500 g of (b) are applied per hectare.

21. A method according to claim 20, wherein from 500 g to 2500 g of (a) and from 25 g to about 200 g of (b) are applied per hectare.

22. A method according to claim 19, wherein the locus is a crop locus.

23. A method according to claim 20, wherein the locus is a crop locus.

24. A method according to claim 21, wherein the locus is a crop locus.

25. A method according to claim 22, wherein the crop is a cereal crop, or sugarcane, and/or (a) is isoproturon, chlortoluron or tebuthiuron.

26. A method according to claim 23, wherein the crop is a cereal crop, or sugarcane, and/or (a) is isoproturon, chlortoluron or tebuthiuron.

27. A method according to claim 24, wherein the crop is a cereal crop, or sugarcane, and/or (a) is isoproturon, chlortoluron or tebuthiuron.

* * * * *